United States Patent [19]

Baden et al.

[11] Patent Number: 4,985,230
[45] Date of Patent: Jan. 15, 1991

[54] METHOD OF CARRYING OUT HETEROGENEOUS CATALYTIC CHEMICAL PROCESSES

[75] Inventors: Niels T. Baden, Virum; Ernst J. Jensen, Frederikssund; Jorgen G. Larsen, Soborg, all of Denmark

[73] Assignee: Haldor Topsoe A/S, Denmark

[21] Appl. No.: 236,897

[22] Filed: Aug. 26, 1988

[30] Foreign Application Priority Data

Aug. 27, 1987 [DK] Denmark .............................. 4481/87

[51] Int. Cl.$^5$ .......................... C01B 3/24; C01B 3/26; C07C 27/06
[52] U.S. Cl. .................................. 423/650; 252/373; 423/652; 423/653; 423/654; 423/659; 423/DIG. 13; 518/715; 518/728; 532/1; 549/248; 549/523; 549/524; 568/449
[58] Field of Search ............. 423/659, 652, DIG. 13, 423/650, 653, 654; 252/373; 549/523, 524, 248; 568/449; 532/1; 518/715, 728

[56] References Cited

U.S. PATENT DOCUMENTS

| 4,407,785 | 10/1983 | Pfefferle | 423/659 |
| 4,671,944 | 6/1987 | Schramm | 423/659 |
| 4,834,962 | 5/1989 | Ludwig | 423/659 |

FOREIGN PATENT DOCUMENTS

0025308 3/1981 European Pat. Off. .

Primary Examiner—Wayne A. Langel
Attorney, Agent, or Firm—Ostrolenk, Faber, Gerb & Soffen

[57] ABSTRACT

A catalytic chemical process is carried out non-adiabatically using as a catalyst a body with two sets of channels throughout the body. One set of channels leads the process fluid towards one of two parallel walls of the catalyst chamber, the other set towards the outer wall, In slits between walls and catalyst heat is exchanged between process fluid and at least one of these walls upon reflecting the process fluid leaving channels of one set and entering channels of the other. The body may be made of alternatingly corrugated and plane sheets using in turn two different orientations for the corrugated sheets. It is preferred that the sheets are arranged orthogonal to the heat transmitting wall(s) and parallel to the overall direction of flow. The method is preferred for endothermic processes, especially steam reforming of hydrocarbon(s).

14 Claims, 5 Drawing Sheets

METHOD OF CARRYING OUT HETEROGENEOUS CATALYTIC CHEMICAL PROCESSES

FIELD OF THE INVENTION

The present invention relates to a method of carrying out catalytic chemical processes at non-adiabatic conditions.

In a heterogeneous catalytic chemical process, a process fluid is contacted with a solid catalyst or a supported liquid phase catalyst which catalyses one or more reactions to form part of the process, the catalyst usually being arranged in one or more beds in one or more catalyst chambers in a catalytic reactor Throughout this specification is by catalytic processes meant processes of this kind.

Carrying out a catalytic process at non-adiabatic conditions implies that during passage of the process fluid through the catalyst bed or beds heat is exchanged between the process fluid and some agent for heating or cooling, usually by convective heat exchange with a heat transmitting wall separating the process fluid from said agent.

By catalyst throughout this specification any solid catalyst or supported liquid phase catalyst is meant, whether in one or more monolithic blocks or in the form of particles. Similarly by catalyst bed a bed is meant in which any such catalyst is placed. By catalyst support body a body is meant which is usable for being transformed into a catalyst, e.g. by impregnation or coating, whether or not the body such treated must undergo one or more further special treatments before reaching an active catalytic state, e.g. calcining or reduction. Similarly, a catalyst as above defined may need a special treatment after being loaded into a catalyst chamber in order to reach an active state By the term fluid both liquids and gaseous substances are aimed at.

Chemical processes may be classified either as endothermic processes, which consume heat, or as exothermic ones, which produce heat.

Among the endothermic catalytic processes of industrial importance and carried out at non-adiabatic conditions, steam reforming of hydrocarbons may be mentioned as an example. It is usually performed at 400°–950° C. The process is often performed in tubes containing a catalyst promoting the reaction(s). The tubes may be arranged in a radiant furnace chamber in which the combustion of a fuel supplies the necessary heat. The process may as an alternative be performed in a heat exchange reformer, e.g. as disclosed in European Patent Application No. 195,688.

Exothermic catalytic processes are often performed at 200°–600° C. As examples of exothermic processes of industrial importance carried out at non-adiabatic conditions, partial oxidations may be mentioned, e.g. the manufacture of ethylene oxide, formaldehyde, or phthalic anhydride. Another example is methanation of carbonoxides. These processes are often performed in cooled tubular reactors.

Some industrially important catalytic processes are reversible and exothermic, e.g. manufacture of ammonia or methanol. These processes are often performed while recirculating a part of the process gas through the catalyst beds as the conversion per pass is often fairly small. A number of different concepts are used among which some are non-adiabatic.

A combination of pressure drop in the process fluid passing through the catalyst bed and heat transfer coefficient between the process fluid and the heat transmitting walls of the catalytic chambers will often represent the limiting process condition for throughput and yield with a given amount of catalyst as well as for process economy. A low pressure drop and a high heat transfer coefficient represent the desired process conditions. A low pressure drop will reduce the power required by the process plant irrespective of type of catalytic process. A high heat transfer coefficient is desirable for all types of non-adiabatic catalytic processes. For endothermic catalytic processes, a high heat transfer coefficient will increase the amount of heat supplied to the process fluid and, therefore, the reaction rate and the degree of conversion for a given amount of catalyst. For exothermic catalytic processes, a high heat transfer coefficient will reduce the temperature of the process fluid and, therefore, the reaction rate. Thus catalyst temperatures are more easily controlled and excess temperatures resulting in catalyst damage are more readily averted. Likewise, undesired reactions, e.g. total oxidations are more easily avoided.

For reversible exothermic catalytic processes, a high heat transfer coefficient between process fluid and cooling surfaces will result in (1) the temperature of the process fluid being reduced and (2) the equilibrium being shifted towards a higher degree of conversion. The total effect will frequently be a higher yield.

Using common commercial catalysts in the form of pellets, rings, or any other particulate form it is not possible to increase the heat transfer coefficient between the walls of the catalyst chamber and the process fluid substantially without simultaneously increasing the pressure drop.

Especially for the steam reforming process, this restriction has been felt. For some time, therefore, various methods using catalyst having non-particulate form have been described, aiming at obtaining simultaneously a low pressure drop and a high heat transfer coefficient.

In the steam reforming process, the highest degree of conversion for a given amount of catalyst is obtained when operating at the highest temperature. For that reason the operation temperature often approaches the upper limit temperature for the tube material. A uniform temperature distribution along the heat transmitting walls will permit the highest average temperature for a given maximum temperature and is, therefore, highly desirable

BACKGROUND OF THE INVENTION

Methods of obtaining some of these features have been described in the literature. Some of these methods utilize bodies which might be used as a catalyst or a catalyst support body if made from a suitable material but which, according to the description in the literature, are used otherwise. Below, references will be given to literature describing catalysts as well as bodies having some of the above features without being catalysts.

U.S. Pat. No. 3,785,620 describes bodies consisting of corrugated lamellae which are proposed used as static mixers.

U.S. Pat. No. 4,296,050 describes packing elements for an exchange column made from a plurality of corrugated plates.

Sales pamphlets from Sulzer Brothers Ltd. describe bodies of similar form as the bodies of the U.S. Patents mentioned above, but in ceramic material, and propose to use them i.a. as catalyst support bodies.

U.S. Pat. No. 3,112,184 describes a method of making ceramic articles some of which have such characteristics as to fulfill the above features if made from a catalytic active material or used as support bodies. Such use is not, however, proposed in the description although it is stated that bodies of a somewhat similar configuration are used in such a way. It is proposed to use the articles for making heat exchangers transferring heat from streams flowing through some channels into streams flowing through others, but not to effect the heat transfer through a vessel wall.

EP Patent Specification No. 0 025 308 discloses a process and an apparatus for endothermic steam reforming of hydrocarbons. A catalyst in the form of a structure comprising a stack of profiled plates is described. The structure is spaced from the walls of the catalyst chamber and has passages angled to the overall direction of flow in the catalyst chamber causing a process fluid to flow alternatively through the catalyst and for a significant length through a space between the structure and the heated walls of the catalyst chamber. Due to this flow pattern, the heated walls will show exended and successive areas of high temperature and low temperature caused by prolonged heating of some of the fluid, and decreasing flow rate in different areas along the reactor walls resulting in low heat transmission, followed by massive flow of the process fluid leaving the catalyst with a reduced temperature due to the reaction inside the catalyst channels.

Thus, since the flow pattern according to the above mentioned EP-patent will not result in a uniform temperature distribution in the fluid entering the catalyst channels at a given level at the catalyst chamber, it is not possible to obtain a uniform catalyst utilization.

A very high transmission of heat from the walls of the catalyst chamber into the process fluid is particularly important when providing some of the heat for steam reforming of hydrocarbons by convective heat exchange between the process fluid and a flue gas in a heat exchange reformer. An essentially even temperature distribution along the heat transmitting walls is also of paramount importance for this process concept.

None of the previously proposed methods has fully overcome the problem of simultaneously obtaining (1) a very low pressure drop in the process fluid passing through the catalyst bed, and (2) a high heat transfer coefficient between the wall(s) of the catalyst chamber and the process fluid, and further (3) having uniform or essentially uniform temperature distribution along the heat transmitting wall(s), and (4) efficient utilization of the total amount of catalyst.

SUMMARY OF THE INVENTION

The object of the present invention is to provide a method which combines a very low pressure drop in the process fluid passing through the catalyst bed and a high and essentially uniform heat transfer coefficient between the wall or walls of the catalyst chamber and the process fluid, combined with an efficient utilization of the catalyst.

Accordingly, the invention relates to a method of carrying out a heterogenous catalytic chemical process at non-adiabatic conditions by passing a stream of a process fluid in one overall flow direction through a catalyst contained in a catalyst chamber defined by walls two of which are substantially uniformly spaced, and transmitting heat through at least one of the two substantially uniformly spaced walls between the process fluids inside the catalyst chamber and a fluid outside the catalyst chamber, said catalyst having a structure of channels arranged in groups of substantially parallel channels causing the process fluid to be subdivided into a plurality of sub-streams having actual flow directions angled to the two uniformly spaced walls and to the overall flow direction, and changing direction whenever reaching one of the walls. The characteristic feature of this method is that the mass flow towards one of the two substantially uniformly spaced walls, at any cross section orthogonal to the overall flow direction, is approximately equal to the mass flow towards the other of said two walls, the flow direction of the sub-streams in one group of channels being different from that in the neighbouring group or groups of channels, and that the actual flow direction of any sub-stream is reflected whenever it reaches one of the two substantially uniformly spaced walls. In this manner there is obtained an essentially uniform temperature distribution along the heat transmitting wall or walls and an efficient utilization of the total amount of catalyst is thus made possible, i.e. that the amount of catalyst necessary for reaching a desired degree of conversion is diminished.

The efficiency of the method according to the present invention results from the immediate reversion of flow of any of the sub-streams whenever such a sub-stream reaches one of the heat transferring walls. No or only a minor flow of the fluid outside the channels and along the heat transferring walls is obtained. This flow pattern provides the least possible distance between cold spots caused by the fluid from the channels outlet and hot spots at the channel inlet. The structure of the catalyst chamber ensures uniform heating of the process fluid due to the frequent and close contact of said process fluid to the heat transferring wall or walls at the points of reflection.

Another feature of the above mentioned catalyst chamber is the continuous and prolonged contact of the process fluid to the catalyst surface obtained by forced angular movement through the catalyst chamber, interrupted only by the reflection points at the heat transferring wall or walls.

DETAILED EXPLANATION OF THE INVENTION

The ratio between the number of sub-streams directed towards each of the two walls can be between 1:100 and 100:1 It is, however, preferred that the ratio is between 1:10 and 10:1. Especially, it is preferred that the number of substreams directed towards one of the substantially uniformly spaced walls are approximately the same as the number of sub-streams directed towards the other of said walls.

It is preferred that the angles between the directions of actual flow through the catalyst and the direction of the overall flow through the catalyst bed are from 5° to 85°, preferably from 15° to 75°, and especially it is preferred that the angles are approximately 45°.

It is preferred to use a catalyst wherein the channels are arranged in layers which are not orthogonal to the overall direction of flow. Especially, it is preferred to use a catalyst wherein the channels are arranged in layers which are approximately parallel to the overall direction of flow.

The manufacture of the catalyst is particularly simple when the layers are angled from 5° to 90° to the heat transmitting wall(s). It is especially preferred that the channels are arranged in layers which are approximately orthogonal to the heat transmitting walls.

An optimum combination of pressure drop and rate of heat transfer results when the streaming process fluid, when reaching whichever of the two uniformly spaced walls, is reflected or thrown back towards the opposite wall in a slit between the wall in question and the catalyst, the width of said slit being less than one fifth of the distance between the two uniformly spaced walls.

In one embodiment of a catalyst chamber complying with the method of the invention, the two substantially uniformly spaced walls are coaxial cylindrical walls, the catalyst chamber being annular and the overall flow direction of the process fluid being parallel to the common axis of the cylindrical walls.

In another embodiment of a catalyst chamber complying with the method of the invention, the two substantially uniformly spaced walls are parallel and plane, the catalyst having the form of a prism with at least one pair of parallel sides The manufacture of a catalyst which may be used in the method of the invention, and the later loading thereof into a catalyst chamber is facilitated when using a catalyst wherein the catalyst is in the form of essentially identical bodies placed in the catalyst chamber in a systematic way.

Complying with the method of the invention, a process fluid can be brought to flow in sub-streams being arranged in sets of layers, the direction of the flow in one set of layers being essentially parallel and different from the direction in the neighbouring set or sets of layers, each set of layers comprising a small number of layers, preferably one or two.

A simple way of obtaining such a flow is by means of a catalyst or catalyst support body comprising layers of sheets defining channels.

The described flow pattern may e.g. be obtained by using as a catalyst or catalyst support body a stack composed of corrugated sheets, preferably alternating with plane sheets. Both types of sheet may, e.g.,be made in a manner known per se and from a material compatible with the catalytic material and the chemical process. The stack may comprise one layer of channels in each set of either streaming direction and take the following form:

a. a corrugated sheet, orientation A
b. a plane sheet
c. a corrugated sheet, orientation B
d. a plane sheet this sequence being repeated until the desired size is obtained. It is not mandatory that all sheets have the same size nor are cut to size along straight lines. Actually, it may often be preferable to cut the plane sheets to a size slightly less than the overall size of the corrugated sheets and/or give them a pair of serrated edges at the sides to become mounted against said walls of essentially constant spacing.

It is suitable to pass the process fluid through a catalyst bed wherein the channels are substantially straight, the angles between the actual directions of the sub-streams and the overall flow direction being 5° to 85°, preferably 15° to 75° and notably approximately 45°.

The flow pattern characteristic for the method of the invention may also be obtained using only corrugated sheets and stacking them using alternately sheets of orientations A and B.

In one of the above mentioned embodiments of a catalyst chamber complying with the method of the invention said two walls are coaxial cylindrical walls. This requires a catalyst in the form of a hollow cylindrical body. A catalyst or catalyst support body of such form producing the flow pattern and heat transmission characterizing the method of the invention may as an example be manufactured by cutting stacks of sheets as described above and placing these stacks within two walls forming an annular mould. The stacks may e.g. be deformed sufficiently for them to attain the form of segments of a hollow cylindrical body and thus fit into the mould. It should be borne in mind that the diameter of the two walls of the mould (corresponding to inner and outer wall, respectively, of a catalyst chamber) usually must differ slightly from the actual diameter of the corresponding walls of the catalyst chamber in order to allow for a possible different thermal expansion for catalyst or catalyst support body and the material of the catalyst chamber and to allow for desired slits between catalyst and walls.

It is especially preferred to stack the sheets defining the stream pattern in the above said mould in such a manner that all flow directions become arranged in planes essentially parallel to the overall direction of flow when the catalyst has been loaded into a catalyst chamber.

The sheets can be stacked orthogonally or obliquely relative to the walls of the above said mould and thus obliquely relative to the heat transmitting walls when the catalyst has become loaded into a catalyst chamber.

The method of the invention is not restricted to the use of bodies prepared from stacks of sheets comprising corrugated sheets or, when using corrugated sheets, to use a special form of corrugation or to use the same form or size of corrugation for all corrugated sheets. Any other means of obtaining said flow pattern while obtaining a transmission of heat between the process fluid and the heat transmitting wall(s) is considered part of the invention when used in carrying out non-adiabatic catalytic processes.

The flow pattern and heat transmission characterizing the method of the invention may e.g. be obtained using instead of sheets a great number of essentially identical pipes placed between two walls of approximately constant spacing of which at least one is heat transmitting. Stacking pipes of e.g. rectangular cross section and having length exeeding the distance between said two walls in such way as to obtain consecutive piles of pipes of alternating orientatiOn, one leading towards one wall, the other towards the other wall, will provide for the desired flow pattern and give rise to only a small pressure drop. Each partial stream leaving a pipe will, when reaching one of the walls reverts towards the other wall through neighbouring pipes of opposite orientation. If the wall is heat transmitting, this reversion causes a high heat transfer coefficient between process fluid and wall.

The flow pattern and heat transfer characterizing the method of the invention may also be obtained e.g. using (instead of pipes) cylinders having two or more fluid passages extending axially therethrough from one end to the other.

In order to transform a catalyst support body providing the desired flow pattern and producing the desired heat transmission into a catalyst usable for carrying out the method of the invention such body may e.g. be impregnated or coated using an impregnation or coating technique and active materials known per se.

The method of the invention may be utilized when carrying out a heterogeneous catalytic chemical process at non-adiabatic conditions and it is not restricted to any particular process.

The process carried out can be an exothermic process, especially partial oxidation of hydrocarbons or alcohols, or hydrocarbon synthesis from carbon oxides and hydrogen.

For partial oxidation of hydrocarbons or alcohols one can, e.g. use a coated catalyst support consisting of for instance glass wool paper, the coating consisting of e.g., approximately 80% (w/w) molybdenum oxide and 20% (w/w) iron oxide promoted with chromium oxide.

Synthesis of hydrocarbons from carbon oxides may be carried out by use of a coated catalyst support body consisting of, e.g. ceramic paper based on alumina fibers, 15 the coating consisting of, e.g 25–50% (w/w) Ni and the balance alumina.

The process carried out can also be an endothermic process, especially steam reforming of hydrocarbons, preferably carried out in a heat exchange reformer.

Such steam reforming may be carried out for instance by use of a coated catalyst support body consisting of, e.g., ceramic paper based on alumina fibers the coating consisting of, e.g., 25% (w/w) Ni, the other main components being magnesia and alumina.

FIGURES OF THE DRAWINGS

The invention is explained below with reference to the drawings, wherein.

The figures are simplified and do not show, e.g., thickness of plane or corrugated sheets The difference between a catalyst and a catalyst support body cannot be discerned from the drawings and the figures do not attempt to make such differentiation.

DETAILED DESCRIPTION OF THE DRAWINGS

Figure 1:
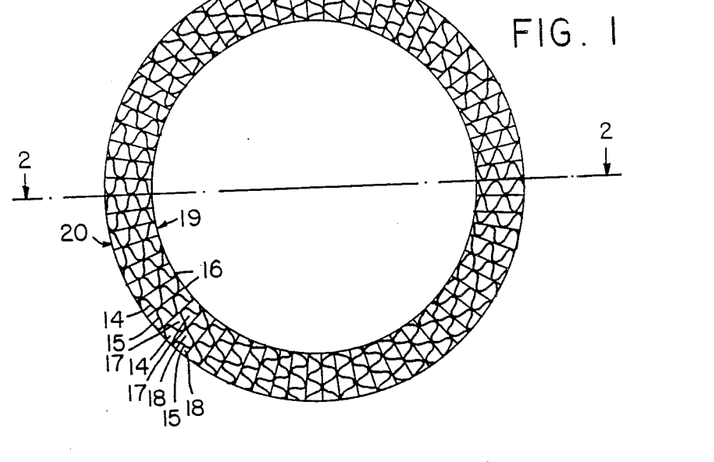
FIG. 1 shows a horizontal section of a catalytic reactor comprising a catalyst bed usable for carrying out the method of the invention.

FIG. 1 shows a horizontal section of a reactor. The reactor has an annular catalyst chamber loaded with a catalyst suitable for carrying out the method of the invention. The process fluid flows down towards the catalyst The catalyst body consists of corrugated sheets 14, 15 and plane sheets 16. The corrugated sheets have alternating orientations. The fluid channels 17 defined by the corrugated sheets 14 and the plane sheets 16 at either side lead fluid flowing down onto the catalyst body towards the outer wall 20 of the catalyst chamber, whereas the fluid channels 18 defined by the corrugated sheets 15 and the plane sheets 16 at either side lead the fluid towards the inner wall 19. In the catalyst shown in the figure, all sheets are essentially orthogonal to the surface of both walls 19, 20.

The slits between catalyst and walls are not shown in FIG. 1.

Figure 2:
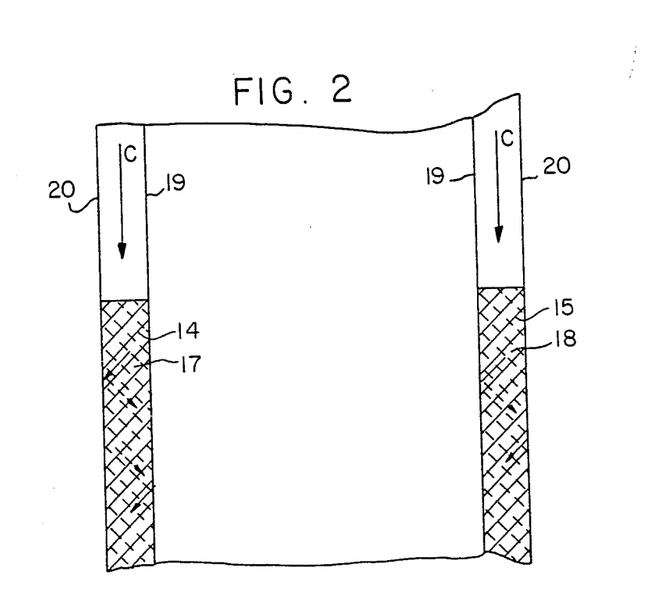
FIG. 2 shows a vertical section of a part of the reactor of FIG. 1 taken along the line a—a.

FIG. 2 shows a vertical section of the top part of the reactor and the catalyst body of FIG. 1 along the line a—a. The overall direction of flow is indicated by the arrows C. All layers of sub-streams and of the channels in which they flow are parallel to the overall direction of flow, C, and being orthogonal to the walls, the plane of a layer will coincide with the cut. The left part of the figure shows a section through a corrugated sheet 14 having sub-streams in channels 17 leading the sub-streams in the direction of the outer wall 20 whereas the right part of the figure shows a section through a corrugated sheet 15 having sub-streams in channels 18 leading the sub-streams in the direction of the inner wall 19. The flow directions of the sub-streams are indicated by arrows. The corrugated sheet lying beneath the sheet being sectioned and the plane sheet in between these sheets is indicated by dashed lines. The flow at this lower level has been indicated by dashed arrows. The flow reflection or "throwing back" upon reaching either of the walls is indicated by shifting from full to dashed arrows at the reversal corresponding to the shifting from the plane of the figure to an underlying plane or vice versa.

The slits between catalyst and walls are not shown in FIG. 2.

The annular catalyst chamber shown in FIGS. 1 and 2 may, e.g., be the catalyst chamber of a heat exchange reformer of the kind disclosed in published European Patent Application No. 195,688.

At or near the edges of sheets against the inner and outer walls zones will occur with little net flow and locally small coefficient of heat transfer. Due to the turbulence caused by the reversal of flow at each or every two sheets or channels these zones will be very narrow and will be situated at distances corresponding to the height of one or two channels, typically a few mm each. The heat conductance in the wall or walls will effectively level out any temperature difference caused by such zones and no uneven temperature distribution will be noticeable.

Figure 3:
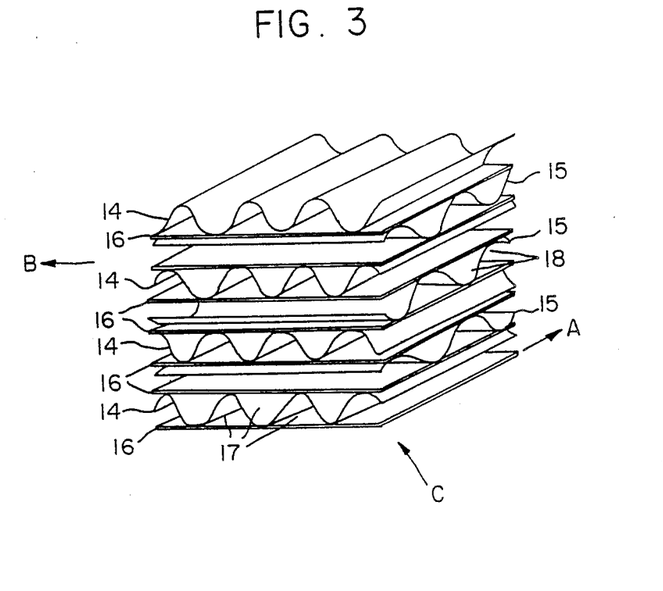
FIG. 3 shows a perspective view of a part of a catalyst or catalyst support body which may be used in carrying out the method of the invention.

FIG. 3 shows a section of a catalyst or catalyst support body which may be used in accordance with the invention. The section consists of a stack of essentially parallel sheets 14, 15, 16, the sheets 14 having a corrugation of orientation A, the sheets 15 having corrugations of orientations B, and the sheets 16 being plane. The stack has been made stacking the sheets in the following order (from below):
one plane sheet 16
one corrugated sheet 14, orientation A
one plane sheet 16
one corrugated sheet 15, orientation B
this sequence being continued throughout the stack The corrugated sheets 14 define together with the plane sheets 16 below and on top of it essentially straight channels 17 and the corrugated sheets 15 define together with the plane sheets 16 below and on top of it essentially straight channels 18 the directions of the two systems of channels 17, 18 being different. The channels of either direction are arranged in essentially parallel layers.

A section as shown in this figure may be made in the catalyst shown in FIGS. 1 and 2, the overall flow direction being indicated by an arrow C e.g. one of the bisectors of the angles formed by the directions of the channels 17, 18. No deformation to accommodate to the loading in an annular catalyst chamber is shown.

Figure 4:
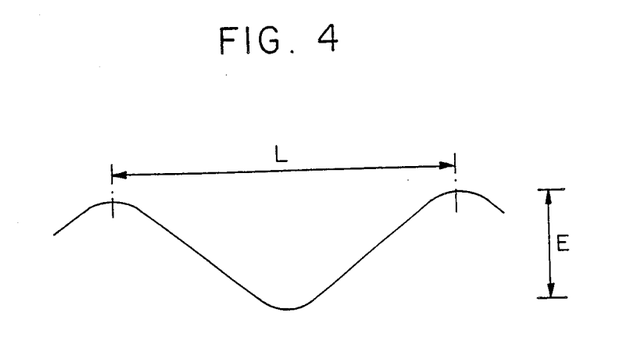
FIG. 4 shows a detail of the body shown in FIG. 3 on an enlarged scale.

FIG. 4 shows an end view of a corrugated sheet seen along the corrugations. The figure indicates the dimensions E and L being characteristic for the corrugation.

Figure 5:
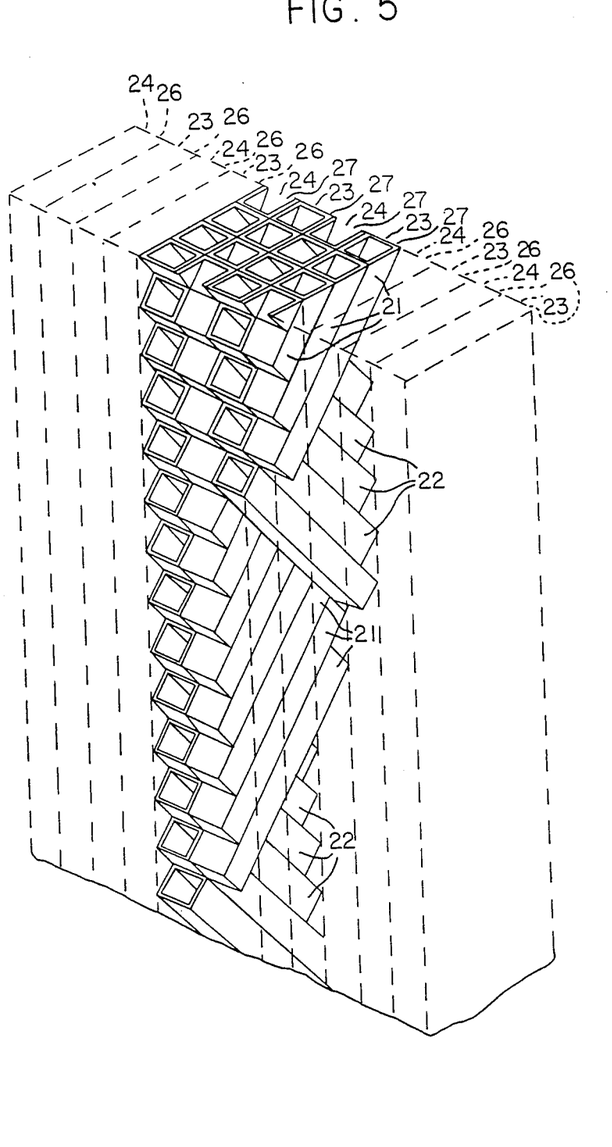
FIG. 5 shows another catalyst or catalyst support body for carrying out the method of the invention from which body a part has been taken away.

FIG. 5 shows a perspective view of another embodiment of a catalyst or catalyst support body suitable for carrying out the method of the invention, a part of the body having been taken away. This body consists of pipes 21, 22 having rectangular cross section. The pipes are stacked in piles 23, 24 with alternating orientation of the pipes, the piles 23 consisting of pipes 21 having an orientation different from that of the pipes 22 of the piles 24, providing for the flow pattern and heat transfer characteristic of the invention. Some of the piles 26 are indicated by dashed lines only, whereas only some of the pipes are shown in the foremost of the piles 27. Although the pipes of different piles are shown reaching the same level, this is not mandatory.

As explained with reference to FIGS. 1 and 2, no uneven temperature distribution will be noticeable at the wall or walls when this embodiment is used for the process.

Figure 6:
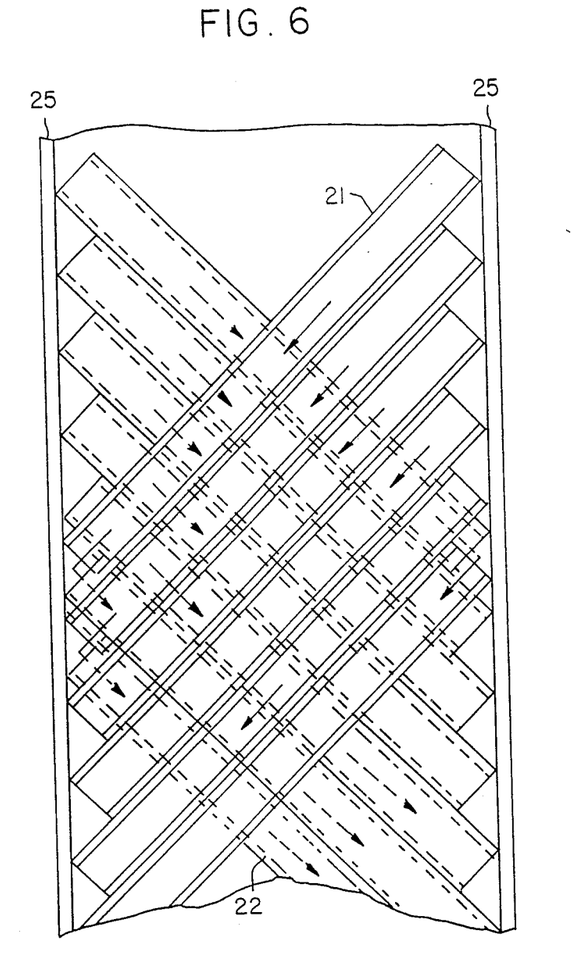
FIG. 6 shows a vertical section of the body of FIG. 5 placed between two walls.

FIG. 6. shows a vertical section of the body of FIG. 5. The body is placed between two walls 25 cutting one pile of pipes 21 and seen orthogonal to the plane of this pile. The pipes of the pile of pipes 22 laying just beneath the layer shown is indicated by dashed lines and the fluid flows are indicated by solid arrows and dashed arrows, respectively The two walls 25 have essentially constant spacing. The reflection of the flows upon reaching these walls is indicated by the arrows.

Figure 7:
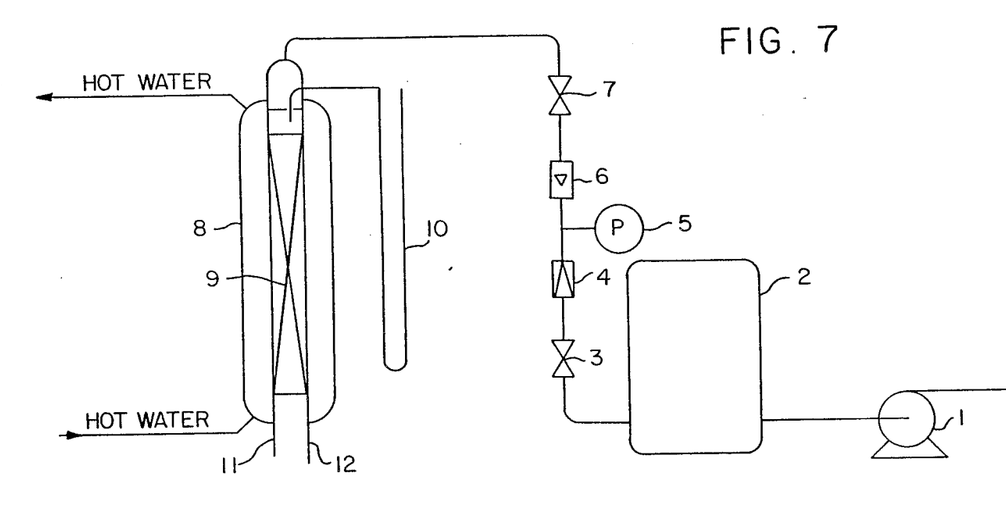
FIG. 7 shows a sketch of the experimental set-up used to determine pressure drops and heat transfer coefficients.

FIG. 7 shows a sketch of the experimental set-up used to determine pressure drops and heat transfer coefficients for different models of catalyst bodies and catalyst particle beds.

The reference numbers of FIG. 7 refer to the following items
  (1) an air compressor, suction capacity $\leq 250$ m³/hr.
  (2) an air vessel
  (3) a closing valve
  (4) a reduction valve
  (5) a precision pressure gauge, 0-15 kg/cm²g
  (6) a flowmeter 0-101 Nm³/hr. at 5 kg/cm²g, 15° C.
  (7) a manually operated regulating valve
  (8) a model of a catalytic reactor having two heat transmitting walls 11, 12 at essentially constant distance. These two walls being plane steel radiators were fitted with wooden laths one at each end, the whole assemble was clamped together. The bottom consisted of a wiremesh screen and the top of an air distributing piece fitted tightly.
  The distance between the radiators could be modified placing sheets of cardboard between one of the radiators and the laths.
  (9) a catalyst body or catalyst bed
  (10) a U-tube manometer The invention and the advantages obtained are explained in more detail in the Example below.

EXAMPLE

In an experimental set-up, models of catalysts providing the characteristics of the invention were compared with specimens of standard catalysts for steam reforming of hydrocarbons.

Three models of cross-arranged corrugated catalyst support bodies were prepared from corrugated cardboard. Models 1 and 2 consisted of cross-arranged corrugated cardboard having a wave height, E, of 2.5 and 4.4 mm and having a plane sheet (a liner), i.e. made up like the body shown in FIG. 3. Model 3 consisted of cross-arranged corrugated cardboard having a wave height, E, of 2.1 mm and not having a liner. For comparison, corresponding experiments were carried out using specimens of standard catalyst rings with OD/ID×H=16.7/7.8×10.4 mm and standard catalyst cylinders with OD×H=5.3×5.1 mm.

The data of the tested catalyst models and catalyst particles are stated in Table 1.

TABLE 1

| Filling | Model 1 | Model 2 | Model 3 | Rings | Cylinders |
|---|---|---|---|---|---|
| Material | Cardboard | Cardboard | Cardboard | Ceramic magnesium aluminate spinel | Ceramic magnesium aluminate spinel |
| E, mm | 2.5 | 4.4 | 2.1 | — | — |
| L, mm | 7.1 | 8.3 | 6.4 | — | — |
| Corrugation Factor | 1.3 | 1.5 | 1.3 | — | — |
| OD, mm | — | — | — | 16.7 | 5.3 |
| ID, mm | — | — | — | 7.8 | — |
| H, mm | — | — | — | 10.4 | 5.1 |
| VOID, % | 82 | 95 | 91 | 52.2 | 34.6 |
| S/V, m²/m³ | 1840 | 1140 | 1240 | 306 | 757 |

The dimensions E and L are indicated in FIG. 4. The corrugation factor is defined as the ratio between the actual upper outer area of the corrugated sheet and the projected area of this sheet on a plane at which the corrugated sheet is brought to rest. S/V is the outer surface (m²) per volume (m³).

It is noted that the outer surface per volume (S/V) is 1.5-2.5 times larger for the cross-arranged cardboard models than for the 5.3×5.1 mm cylinders. Thus, for the reforming process it is expected that the catalyst activity per volume will be higher when using a cross-arranged catalyst than when using 5.3×5.1 mm catalyst cylinders, since the effectiveness factor of the reforming reaction is very low, typically less than 5%, in the bottom 80% of an ordinary tubular reformer and decreasing to less than 1% at the bottom, cf. J. R. Rostrup-Nielsen, Catalytic Steam Reforming, Springer Verlag, Berlin (1984), p. 69.

The heat transfer and pressure drop properties of the models and of the catalyst cylinders and rings were determined in a 1000 mm long vertical channel having 55×300 mm rectangular horizontal cross section. The two walls of 300×1000 mm were two parallel plane radiators wherein hot water at 80° C. was circulated. The cardboard models of dimensions 55×300×1000 mm were arranged having the planes of the sheet orthogonal to the heating surfaces and parallel to the direction of overall flow. The distance between the radiators could be increased at will as above said.

FIG. 7 shows a sketch of the experimental set-up. When carrying out an experiment, a stream of air was passed down through the channel containing a cardboard model or catalyst cylinders or rings. The pressure drop across the "catalyst filling" and the heat transfer were determined. Valve (3) was opened and the reduction valve (4) and the control valve (7) were adjusted to obtain a reading on the pressure gauge (5) of 6 kg/cm²g and the flowmeter (6) showed a predetermined reading. The pressure drop across the catalyst filling (9) indicated by the U-tube manometer (10) was read The temperatures of the catalyst or cardboard model and the hot water were recorded at 5–10 minute intervals until the recorded temperatures were stable. The difference between the hot water temperature at inlet and outlet was less than 2° C. in all experiments. In the interpretation of the measurements it was assumed that the temperature was the same in all positions on the radiator walls.

The physical properties of the gas flow of the experiments are stated in the below Table 2.

TABLE 2

| | | |
|---|---|---|
| G, | Mass Flux, kg/m²/h | $7.2 \times 10^3$ |
| | Viscosity, kg/m/h | 0.070 |
| k, | Conductivity, kcal/m/h/°C. | 0.023 |
| $C_p$, | Heat Capacity, kcal/kg/°C. | 0.24 |
| | Gas Density, kg/m³ | 1.09 |

Thirteen thermocouples were placed in the catalyst or models.

In the experiments using catalyst rings or cylinders, the distance between the radiator walls was 60 mm and all the thermocouples were placed in the centre plane between the two radiator walls. One thermocouple was placed on the centre line 10 mm from the bottom (gas outlet) and the remaining 12 were placed 10, 125, 250, and 500 mm from the top and in three different lateral positions: On the centre line 95 mm to the left, and 95 mm to the right.

In the experiments testing the cardboard models, all thermocouples - except two - were placed in the centre plane orthogonal to the radiator walls. Five thermocouples were placed on the centre line 10 mm from the bottom (gas outlet) and 10, 125, 250, and 500 mm from the top. Six thermocouples were placed 19.5 mm from the centre line 125, 250, and 500 mm from the top, three on the near side of the centre plane between the two radiator walls and three on the far side. The remaining two thermocouples were placed in the centre plane between the two radiator walls 250 mm from the top and 105 mm from the centre line, one to the left and one to the right.

The results obtained in the various experiments are summarized in Table 3.

TABLE 3

Determinations of Heat Transfer Coefficient, h, and Pressure Drop per m of Filling, $\frac{dP}{dZ}$.

| Filling | Slit between wall and filling, mm | h, $\frac{kcal}{m^2 hr \, °C.}$ | $\frac{dP}{dZ}$, mm H₂O/m |
|---|---|---|---|
| Model 1 | 1.2 | 163 | 81 |
| | 2.4 | 117 | 72 |
| Model 2 | 0.6 | 230 | 182 |
| | 1.2 | 187 | 49 |
| | 2.4 | 122 | 34 |
| Model 3 | 0 | 193 | 133 |
| | 0.6 | 196 | 107 |
| | 1.2 | 161 | 93 |
| Standard Catalyst | 0 | 152 | 245 |

TABLE 3-continued

Determinations of Heat Transfer Coefficient, h, and Pressure Drop per m of Filling, $\frac{dP}{dZ}$.

| Filling | Slit between wall and filling, mm | h, $\frac{kcal}{m^2 hr \, °C.}$ | $\frac{dP}{dZ}$, mm H₂O/m |
|---|---|---|---|
| Ring, 16.7/7.8 × 10.4 mm Standard Catalyst Cylinder, 5.3 × 5.1 mm | 0 | 152 | 1441 |

The pressure drops found for the cardboard models are lower, in some cases an order of magnitude lower than those found for the catalyst particles.

The heat transfer coefficients found for the cardboard models are higher than those found for the catalyst particles, provided that the slit width between the specimen and the wall does not exceed 1.2 mm.

Comparing the experimental results found using models 1 and 2, it is seen that reducing the channel width leads to superior heat transfer and pressure drop properties.

Comparing the experimental results found for models 2 and 3, it is seen that the pressure drop may be halved by replacing a catalyst or catalyst support body (model 3) having no liner by a catalyst or a catalyst support body (model 2) having a liner, having the same outer surface per volume (S/V) and yielding the same heat transfer coefficient when using the same slit width.

In the above explanations referring to the figures and in the above Example, a number of embodiments of a catalyst complying with the method of the invention have been described in detail and the experimental results found when comparing three of these embodiments with a standard catalyst in a model experiment are stated. However, the results are considered illustrating only and not restricting the method of the invention to the specifically described embodiments. Any means of realizing the flow pattern and heat transferring characteristic of the invention and usable for carrying out a heterogeneous catalytic chemical process at non-adiabatic conditions is considered part of the invention only being restricted by the scope of the appended claims.

Using stacks of corrugated sheets having undulating corrugations will fully comply with the method of the invention.

Also corrugated sheets (having straight or undulating corrugations) may be given a secondary corrugation, optionally having other form or size and an orientation different from the primary corrugation may be used according to the invention.

Further possibilities comprise apertured sheets or sheets having surface projections.

What we claim:

1. In a method of carrying out a heterogeneous catalytic chemical process at non-adiabatic conditions by passing a stream of a process fluid in one overall flow direction through a catalyst contained in a catalyst chamber defined by walls two of which are substantially uniformly spaced, and transmitting heat through at least one of the two substantially uniformly spaced walls between the process fluid inside the catalyst chamber and a fluid outside the catalyst chamber, said catalyst having a structure of channels arranged in groups of substantially parallel channels causing the process fluid to be subdivided into a plurality of sub-streams having actual flow directions angled to the two uniformly spaced walls and the overall flow direction, and changing direction whenever reaching one of the walls, the improvement which comprises that the mass flow towards one of the two substantially uniformly spaced walls, at any cross section orthogonal to the overall flow direction, is approximately equal to the mass flow towards the other of said two walls, the flow direction of the sub-streams in one group of channels being different from that in the neighboring group or groups of channels, and that the actual flow direction of any sub-stream is changed whenever it reaches one of the two substantially uniformly spaced walls in leaving a channel and entering neighboring channels, so as to direct the sub-stream towards the other of said substantially uniformly spaced walls.

2. A method as claimed in claim 1, wherein the number of sub-streams directed towards one of the substantially uniformly spaced walls is approximately the same as the number of sub-streams directed towards the other of said walls.

3. A method as claimed in claim 1, wherein there is used a catalyst the channels of which are arranged in layers which are approximately parallel to the overall direction of flow.

4. A method as claimed in claim 1, wherein there is used a catalyst the channels of which are all arranged in layers which are approximately orthogonal to the heat transmitting wall or walls.

5. A method as claimed in claim 1, wherein there is used a catalyst chamber in which the two substantially uniformly spaced walls are coaxial cylindrical walls, the catalyst chamber being annular and the overall flow direction of the process fluid being parallel to the common axis of the cylindrical walls.

6. A method as claimed in claim 1, wherein there is used a catalyst chamber in which the two substantially uniformly spaced walls are parallel and plane, the catalyst having the form of a prism with at least one pair of parallel sides.

7. A method as claimed in claim 1, wherein there is used a catalyst wherein the catalyst is in the form of essentially identical bodies positioned in the catalyst chamber in a systematic way.

8. A method as claimed in claim 1, wherein the chemical reaction is an endothermic reaction.

9. A method as claimed in claim 8, wherein the chemical reaction is steam reforming of hydrocarbons.

10. A method as claimed in claim 9, wherein the steam reforming of hydrocarbons is carried out in a heat exchange reformer.

11. A method as claimed in claim 1, wherein the chemical reaction is an exothermic reaction.

12. A method as claimed in claim 11, wherein the exothermic reaction is a partial oxidation of hydrocarbons.

13. A method as claimed in claim 11, wherein the exothermic reaction is a partial oxidation of at least one alcohol.

14. A method as claimed in claim 11, wherein the exothermic reaction is a hydrocarbon synthesis from carbon oxides and hydrogen.

* * * * *